US010251973B2

(12) United States Patent
Lam et al.

(10) Patent No.: US 10,251,973 B2
(45) Date of Patent: Apr. 9, 2019

(54) ADHESIVE COMPOSITION AND WOUND DRESSINGS OR OSTOMY APPLIANCES COMPRISING SUCH ADHESIVE COMPOSITION

(75) Inventors: Peter Kwok Hing Lam, Frederiksberg (DK); Mads Lykke, Bronshoj (DK)

(73) Assignee: Coloplast A/S, Humlebaek (DK)

( * ) Notice: Subject to any disclaimer, the term of this patent is extended or adjusted under 35 U.S.C. 154(b) by 2337 days.

(21) Appl. No.: 10/583,345

(22) PCT Filed: Dec. 16, 2004

(86) PCT No.: PCT/DK2004/000877
§ 371 (c)(1),
(2), (4) Date: Jun. 19, 2006

(87) PCT Pub. No.: WO2005/059054
PCT Pub. Date: Jun. 30, 2005

(65) Prior Publication Data
US 2009/0149567 A1     Jun. 11, 2009

(30) Foreign Application Priority Data
Dec. 19, 2003 (DK) .................. 2003 01904

(51) Int. Cl.
A61L 15/58     (2006.01)
A61L 24/04     (2006.01)
A61L 24/08     (2006.01)
C09J 153/00    (2006.01)
C09J 153/02    (2006.01)

(52) U.S. Cl.
CPC .......... A61L 15/585 (2013.01); A61L 24/046 (2013.01); A61L 24/08 (2013.01); C09J 153/00 (2013.01); C09J 153/02 (2013.01); C08L 2666/02 (2013.01); C08L 2666/04 (2013.01)

(58) Field of Classification Search
CPC ...... A61L 15/585; A61L 24/046; A61L 24/08; C09J 153/00; C09J 153/02; C08L 2666/02; C08L 2666/04
USPC ..... 525/80, 90, 92 R, 98, 99, 191, 241, 244, 525/332.9, 333.1, 333.3
See application file for complete search history.

(56) References Cited

U.S. PATENT DOCUMENTS

| | | | |
|---|---|---|---|
| 3,339,549 A | 9/1967 | Morse | |
| 3,908,658 A | 9/1975 | Marsan | |
| 4,022,723 A | 5/1977 | Hokama et al. | |
| 4,231,369 A * | 11/1980 | Sorensen et al. | 604/336 |
| 4,367,732 A | 1/1983 | Poulsen et al. | |
| 4,551,490 A * | 11/1985 | Doyle et al. | 524/22 |
| 4,797,322 A | 1/1989 | Huddleston et al. | |
| 5,006,401 A | 4/1991 | Frank | |
| 5,051,259 A | 9/1991 | Olsen et al. | |
| 5,109,874 A * | 5/1992 | Bellingham et al. | 128/888 |
| 5,463,187 A | 10/1995 | Battle | |
| 5,492,943 A | 2/1996 | Stempel | |
| 5,760,135 A * | 6/1998 | Korpman et al. | 525/95 |
| 6,303,700 B1 | 10/2001 | Chen | |
| 6,326,421 B1 | 12/2001 | Lipman | |
| 6,451,883 B1 * | 9/2002 | Chen | A61F 5/443 523/111 |
| 6,458,886 B1 | 10/2002 | Nielsen et al. | |
| 6,482,281 B1 | 11/2002 | Schmidt | |
| 6,509,391 B2 | 1/2003 | Gothjaelpsen et al. | |
| 6,558,792 B1 * | 5/2003 | Vaabengaard et al. | 428/355 CP |
| 6,583,220 B1 | 6/2003 | Lipman | |
| 6,706,813 B2 | 3/2004 | Chiba et al. | |
| 2002/0077420 A1 * | 6/2002 | Chiba | C08L 23/10 525/89 |
| 2002/0120032 A1 * | 8/2002 | Gothjaelpsen et al. | 523/111 |
| 2003/0195287 A1 | 10/2003 | Fisher | |
| 2005/0080155 A1 * | 4/2005 | Fattman et al. | 523/105 |

FOREIGN PATENT DOCUMENTS

| | | | |
|---|---|---|---|
| EP | 0 319 236 A2 | 6/1989 | |
| EP | 0 370 789 A2 | 5/1990 | |
| EP | 0 479 311 A2 | 4/1992 | |
| EP | 0479311 A2 * | 4/1992 | ............ C09J 153/00 |
| EP | 479311 A2 * | 4/1992 | ............ C09J 153/00 |
| EP | 1 195 405 A1 | 4/2002 | |
| JP | 61 235451 | 10/1986 | |
| JP | 2002 161186 | 6/2002 | |
| WO | WO 89/05619 | 6/1989 | |
| WO | WO 98/17329 | 4/1998 | |

* cited by examiner

Primary Examiner — Robert S Jones
(74) Attorney, Agent, or Firm — Coloplast Corp., Coloplast A/S; Nick Baumann

(57) ABSTRACT

An adhesive composition of a rubbery elastomeric matrix comprising a block-copolymer and a homopolymer where the block-copolymer contains one or more block(s) of a polymerized mono alkenyl arene monomer and one or more block(s) consisting of a linear or branched saturated hydrocarbon chain wherein the homopolymer is a linear or branched saturated hydrocarbon chain made from the same monomer as said block(s) consisting of a linear or branched saturated hydrocarbon chain.

24 Claims, No Drawings

ADHESIVE COMPOSITION AND WOUND DRESSINGS OR OSTOMY APPLIANCES COMPRISING SUCH ADHESIVE COMPOSITION

This is a nationalization of PCT/DK04/000877 filed Dec. 16, 2004 and published in English.

BACKGROUND OF THE INVENTION

1. Field of the Invention

The present invention relates to pressure sensitive adhesive compositions suitable for various medical applications and especially suitable for use for adhesion to the skin. The adhesive composition may be used for securing ostomy appliances to the skin and for sealing around a stoma, for securing wound dressings or wound drainage bandages to the skin, for securing devices for collecting urine to the skin, or for securing orthoses or prostheses to the skin. More specifically, the invention relates to adhesive compositions comprising a rubbery elastomeric matrix comprising a block-copolymer and a homo-polymer, the use of such adhesive compositions for the preparation of a wound dressing or an adhesive wafer for an ostomy appliance, and to wound dressings or ostomy appliances comprising such adhesive composition.

2. Description of the Related Art

Various skin adhesive agents are used today for the above-mentioned purposes. Some of these skin adhesive agents comprises a self-adhesive elastomeric matrix, in which water absorbing, swelling particles, the so-called hydrocolloids, are dispersed.

Thus, U.S. Pat. No. 3,339,549 discloses a blend of a rubbery elastomer such as polyisobutylene and one or more water-soluble or water swellable hydrocolloids such as a powdery mixture of pectin, gelatine and carboxymethylcellulose. The adhesive mass has a water-insoluble film applied to one surface. A composition of this type is available commercially from E. R. Squibb & Sons Inc. under the trademark "Stomahesive" and is used as a skin barrier around stomas to prevent skin breakdown by the corrosive fluids discharged by the stoma.

In adhesive compositions of this type, the polyisobutylene is responsible for provision of the adhesive properties and the dispersed hydrocolloid powders absorb fluid and render the adhesive agent capable of also adhering to moist skin (wet tack). These compositions are also gaining increasing acceptance as wound dressings for dermal ulcers, burns and other exuding wounds.

One major problem which has been encountered with conventional adhesive compositions comprising hydrocolloids is their susceptibility to breakdown upon exposure to body fluids. When the compositions are used as skin barriers, e.g., around stomas, absorption of fluid is desirable, but excessive swelling causes the composition to lose its integrity, opening for leaks, and the barrier must be replaced more often than is desirable from a skin protection point of view, and very often, a residue remains on the skin, which in many cases is difficulty to remove.

A number of attempts have been made to improve the properties of the adhesive compositions in order to overcome the above-mentioned drawbacks.

Thus, incorporation of styrene copolymers have been disclosed in a number of patent references.

Thus, U.S. Pat. No. 4,231,369 disclose an ostomy skin barrier consisting of a styrene copolymer having dispersed therein a water-soluble hydrocolloid gum and a tackifier.

In U.S. Pat. No. 4,367,732 disclose an ostomy skin barrier consisting of a water soluble hydrocolloid dispersed in a continuous phase consisting of a styrene copolymer, a hydrocarbon tackifier, and a plasticizer, an antioxidant, and an oily extender.

U.S. Pat. No. 4,551,490 discloses medical grade pressure sensitive adhesive compositions comprising a homogeneous mixture of 5-30% of one or more polyisobutylenes, 3-20% of one or more styrene radial or block type copolymers having a content of diblock copolymer below 20%, mineral oil, one or more water soluble hydrocolloid gums, and a tackifier. One or more water swellable cohesive strengthening agents, an antioxidant, and various other ingredients may also be included within the adhesive composition.

U.S. Pat. No. 5,492,943 discloses a pressure sensitive adhesive composition including a blend of two viscoelastic adhesive elastomers, specifically, high molecular weight polyisobutylene and a styrene block copolymer, which along with a plasticizer (preferably petrolatum) and a suitable tackifier and antioxidant, form a continuous phase in which hydrocolloids such as sodium carboxymethylcellulose and pectin are dispersed. The adhesive compositions are stated to be useful for wafers for adhering ostomy appliances to the skin and differ from known compositions by comprising styrene block-copolymers having a higher content of diblock copolymer, completely avoiding the use of low molecular weight polyisobutylene and furthermore by preferably not including gelatine.

WO 98/17329 discloses adhesive compositions comprising below 20% of styrene copolymer having a major content of diblock copolymer and furthermore comprising a tackifying liquid constituent.

Adhesives based on three-block styrene-isoprene-styrene (SIS) copolymers are highly elastic and show a very high degree of cohesion. Traditional SIS-based adhesives are all modified using a resin and plasticizer to obtain a suitable balance between the plastic and elastic properties in order to obtain satisfactory adhesiveness and, at the same time, sufficient plasticity which implies that the adhesive is able to adapt to the structure and shape of the skin surface and follow the movements of the skin without loosing the grip.

In order to increase the softness, it is normal to use a considerable amount of plasticizer such as Dioctyl Adipate (DOA) or Dioctyl Phthalate (DOP). These plasticizers may leach out or migrate and come into contact with the skin or a wound and cause adverse reactions, or they may migrate into the backing material causing performance and storage problems. Many plasticizers are claimed to have a negative impact on the health.

Lower molecular weight copolymers may be used as plasticizers or extenders. These may, however, cause cohesion problems within the adhesive leading to a too soft material with the tendency to cohesive break when peeled from the skin leaving residues on the skin.

Lower molecular weight homo-polymers of polyisobutylene or polybutylene maybe used to modify the properties of SIS based adhesives. However, these homopolymers are not fully compatible with the isoprene phase of the block copolymers they are intended to modify. Consequently, a multiphase polymer system is produced having rheological and mechanical properties being difficult to control sufficiently for obtaining a satisfactory cohesion and suitable flowing properties.

Furthermore, SIS copolymers contain unsaturated chemical bonds and are therefore prone to yellowing and deterioration during processing due to exposure to radiation such as light or radiation sterilization and on long-term storage.

Loss or lack of cohesion, poor deterioration resistance when moisture has been absorbed combined with the risk of leaving residues on the skin are some of the greatest failings of current commercial medical adhesives.

Homo- or di block polymers of higher molecular weight can also be used for adhesive compositions. Unless cross-linking can occur, they are however more difficult to formulate to give a suitable balance of properties rendering the adhesive compositions suitable for use as medical pressure sensitive adhesives.

Styrene-isobutylene copolymers as such are known. They are known as random copolymers, which cannot form physically cross-linked domains as the styrene blocks of di, tri or multi block styrene copolymers, and are therefore of limited interest due to poor fulfillment of properties desirable in adhesives.

Thus, U.S. Pat. No. 4,022,723 discloses a pressure sensitive adhesive using a terpolymer of styrene, isobutylene and beta-pinene. The terpolymer is a random copolymer of low molecular weight of from 1500 to 7000. It is claimed to be suitable as a tackifier resin.

U.S. Pat. No. 3,908,658 discloses a seal and appliance system for ostomy patients. A low molecular weight styrene-isobutylene copolymer is used together with an ethylene-vinyl acetate copolymer and mineral oil. The styrene-isobutylene copolymer used is a random copolymer, supplied by Velsico under the trade name Klyrvel 90 comprising 90% styrene and 10% isobutylene. These copolymers are known to have molecular weight of 6000 to 12000. The high content of styrene indicates that it is a hard material lacking in flexibility and elasticity.

JP Patent No. 61235451 discloses the use of liquid styrene-isobutylene copolymer as a softener for Styrene Butadiene Compounds (SBC) in hydrophobic adhesives. Diblock copolymers do not provide physical cross-linking and are therefore not elastomers. This polymer will require addition of cohesion strengtheners, such as SIS or styrene-isobutylene-styrene (SIBS) elastomers for obtaining a good adhesive formulation.

New polymerisation methods have now been developed and enabled the production of styrene-isobutylene-styrene tri- or higher block copolymers, including star copolymers, having various molecular weights and styrene content.

The use of these polymers is disclosed in JP patent application No. 2002-161186, disclosing SIBS block copolymers, which can be used in combination with other cross-linkable styrene block copolymers for improved flexibility, mechanical strength, gas-barrier properties and mouldability, and are suitable for sealing material requiring good permanent compression properties. JP patent application No. 2002-161186 is silent with respect to the use of such copolymers in adhesive compositions.

It has now surprisingly been found that SIBS may be used for formulating soft adhesive formulations without compromising the tensile strength. It has also been found that SIBS offers superior softness and barrier properties. The polyisobutylene block, being a saturated chain, provides superior resistance against yellowing and deterioration and it has been found that the polyisobutylene block imparts new properties to the adhesive composition rendering the adhesive more suitable for use as skin adhesive.

Furthermore, it has surprisingly been found that it is possible to control the properties of the adhesive composition by controlling the content of PIB (polyisobutylene) homo-polymers in the soft domain of SIBS. There is good compatibility between the soft segment of the block copolymer and the homo-polymer. With such combinations, properties may be obtained, which have only been partially achievable by SIS copolymers or polyisobutylene homopolymers or combinations thereof.

It has surprisingly been found that a combination of a block copolymer, which contain at least one block of a polymerised monoaryl alkene and at least one block of a straight or branched saturated hydrocarbon chain, such as a SIBS block copolymer, and a homopolymer prepared from the same monomer as the block(s) of a straight or branched saturated hydrocarbon chain and having the same chemical structure, such as PIB (polyisobutylene polymer), it is possible to prepare an adhesive composition for skin application without the use of conventional plasticizers normally used in connection with styrene copolymers in adhesive compositions.

SUMMARY OF THE INVENTION

Thus, the present invention relates to an adhesive composition comprising a rubbery elastomeric matrix comprising a block-copolymer and a homopolymer wherein the block-copolymer contains one or more block(s) of a polymerised mono alkenyl arene monomer and one or more block(s) consisting of a linear or branched saturated hydrocarbon chain, wherein the homopolymer is a linear or branched saturated hydrocarbon chain made from the same monomer as said block(s) consisting of a linear or branched saturated hydrocarbon chain.

Still further, the invention relates to a wound dressing or an adhesive wafer for an ostomy appliance comprising such an adhesive composition.

DETAILED DESCRIPTION OF THE PRESENT INVENTION

Thus, the present invention relates to an adhesive composition comprising a rubbery elastomeric matrix comprising a block-copolymer and a homo-polymer wherein some of the blocks in the block-copolymer and the homopolymer have the same chemical structure, albeit they may be of different molecular weight, i.e. the linear or branched saturated hydrocarbon chain in the block copolymer contain the same repeating chemical unit as in the homopolymer.

According to one embodiment of the invention, the block copolymer is a di, tri, or multiblock co-polymer, preferably a tri, or a multiblock co-polymer, or most preferred a tri-block copolymer. Suitably, the tri-block copolymer is an ABA block copolymer, where A designates a block of a polymerised mono alkenyl arene monomer and B a block of a linear or branched saturated hydrocarbon chain.

Suitably, the tri or multiblock copolymers used according to the invention, contain at least two A blocks, where A designates a block of a polymerised mono alkenyl arene monomer.

It is preferred that the block-copolymer comprises blocks capable of forming a physically cross-linked matrix and it is suitably selected from block-copolymers comprising styrene blocks and one or more olefine blocks being suitable for use in medical adhesives.

Thus, in one embodiment of the invention, the polymerised mono alkenyl arene monomer form a polystyrene block.

Suitably, the block copolymer is a styrene-isobutylene-styrene (SIBS) block copolymer.

In a further embodiment of the invention, the rubbery elastomeric matrix comprises polybutylenes or polyisobutylene, preferably polyisobutylene.

Suitably, the block consisting of a linear or branched saturated hydrocarbon chain is a polyisobutylene block and the homopolymer is polyisobutylene.

Thus, it has been found that there is significantly reduced disruption of the physical cross-linking in the SIBS network from the PIB polymer as compared with a SIS network. This gives rise to increased cohesion in the adhesive. Most surprisingly, it has been found that the gel strength and deterioration resistance of the adhesive(s) are improved. Without limiting the invention to any specific theory it is believed that this may be because of better cohesion and compatibility.

Further it has surprisingly been found that adhesives formulated from SIBS block copolymer and PIB homopolymer are much more transparent than equivalent formulations from SIS block copolymers and PIB homo-polymers. Without limiting the invention to any specific theory it is believed that this may be due to complete compatibility of the soft domain in the block copolymer and the PIB homopolymer and because the domains of polystyrene clusters are too small to interfere with visible light. The more transparent appearance in medical adhesives can offer an aesthetic appeal and more confidence in use to patients.

Furthermore, because of the fully saturated nature of the polymer, when processed at high temperatures in medical adhesive formulations, there is a reduced tendency to yellowing as is seen in SIS adhesives. The yellowing in conventional formulations sometimes causes concern over the reproducibility and stability of the adhesive.

The block(s) of a polymerised mono alkenyl arene monomer suitably has a molecular weight between 1000 and 10,000.

The block(s) consisting of a linear or branched saturated hydrocarbon chain suitably has a molecular weight between 20,000 and 100,000.

Suitable SIBS copolymers are such having a molecular weight Mw of from about 50,000 to about 150,000 or even up to 300,000 or 500,000.

The homopolymer suitably has a molecular weight between 20 000 and 100 000

In one embodiment of the invention the adhesive composition comprises from 1-70% by weight of the composition of the block-copolymer and up to 70% by weight of the composition of the homo-polymer.

The adhesive composition of the invention may also comprise water absorbing and water swelling hydrocolloids, suitably in the form of particles.

The presence of hydrocolloid particles being characterized by rapid swelling under influence of water may further improve moisture uptake and transmission. A disadvantage may be the lack of complete coherence at high loads of hydrocolloid particles of such adhesives when immersed in water over time, but this may be compensated by a desired absorption capacity.

The addition of hydrocolloid particles will preferably be in the range of 5-60% by weight but will not be limited to this range.

The total amount of hydrocolloids are typically 5-55% by weight of the total composition, more preferred 5-45% by weight, and preferably from 30 to 40% by weight of the total composition.

The hydrocolloids are suitably naturally occurring hydrocolloids such as guar gum, locust bean gum, pectin, alginates, gelatin, xanthan or karaya gum, semi synthetic hydrocolloids such as cellulose derivatives, e.g. salts of carboxymethylcellulose, methylcellulose and hydroxypropyl methylcellulose, sodium starch glycollate and synthetic hydrocolloids such as polyvinyl pyrrolidone, polyvinyl alcohol, polyethylene glycol or certain polyacrylates. Suitably the hydrocolloids is in the form of particles.

It is often suitable to use a combination of two or more hydrocolloids such as a combination of pectin, gelatine and carboxymethylcellulose as the hydrocolloid component.

A particularly preferred composition according to the invention comprises a mixture of polyisobutylene, SIBS and CMC.

Thus, in a further embodiment, the adhesive composition of the invention comprises from 1-70% by weight of the composition of the block-copolymer and up to 70% by weight of the composition of a homopolymer, and from 5-60% by weight of one or more hydrocolloids.

In still a further embodiment of the invention, the adhesive composition comprises a substantially homogeneous mixture of 25-60% of one or more polyisobutylenes, 3-35% of one or more styrene block copolymers comprising polyisobutylene block(s), and 20-60% of one or more hydrocolloids.

A plasticizer may typically be present in an amount of from 0% to about 40% by weight of the total composition. The plasticizer used in such compositions are suitably a plasticizer for the block(s) of polymerized monoalkenyl arene, e.g. polystyrene, such as DOA or DOP.

The adhesive compositions may e.g. be based on a SIBS block copolymer containing DOA or DOP as the plasticizer.

Paraffin oil may be present for providing softness to the adhesive composition and may be present in an amount from 5% to 25%, typically in an amount of about 15% by weight of the total composition.

In a further embodiment of the invention the composition comprises a tackifier resin.

The tackifying resin optionally used in accordance with the invention is preferably a hydrocarbon tackifier resin and is more preferred selected from the group comprising polymers and copolymers of cyclopentadiene, dicyclopentadiene, alphapinene or beta-pinene. A tackifier resin may be present in an amount of from 0 to 40% by weight of the total composition The adhesive compositions of the invention may optionally comprise further components normally used in formulation of adhesive compositions e.g. pigments such as zinc oxide or titanium dioxide. Pigments may be present in amount up to about 5% and will typically be present in an amount of 2-4%.

Thus in another embodiment, the adhesive composition according to the invention comprises a substantially homogeneous mixture of 5-60% of a rubbery elastomeric matrix comprising a block copolymer and a homo-polymer as described above, 5-60% of one or more hydrocolloids comprising, 0-25% of one or more tackifier resins, 0-10% of a plasticizer and 0-5% pigment.

In still another embodiment, the invention relates to an adhesive composition comprising from 1 to 70% by weight of the composition of a tri or multi-block copolymer containing one or more block(s) of a polymerised mono alkenyl arene monomer and one or more block(s) consisting of a linear or branched saturated hydrocarbon chain, up to 70% by weight of the composition of a second tri, or multi-block copolymer, suitably but not necessarily containing one or more block(s) of a polymerised mono alkenyl arene monomer and one or more block(s) consisting of a linear or branched saturated hydrocarbon chain, a homopolymer, and from 5 to 60% by weight of the composition of one or more hydrocolloids.

The second three or multi-block copolymer suitably has a molecular weight Mw of from 1000 and up to about 300,000.

Such compositions may e.g. be based on a SIBS block copolymer, a second SIBS or a SIS block copolymer and may also contain a plasticizer such as DOA or DOP.

The adhesive compositions of the invention are especially suitable for use for medical appliances such as ostomy bags, wound dressings, IV-fixations, adhesive surgical drapes, skin fixation of continence catheters, drains, breast prosthesis and monitoring devices. But the purpose of the adhesive of the invention also relates to attachment of any other item to the skin of any mammal. Further as secondary fields the adhesive will be suited for a wide number of industrial applications like for labels and stickers that, due to their moisture sensitivity, should be easy to remove when wet.

The invention also relates to an ostomy appliance with an adhesive wafer comprising an adhesive composition as described above.

An ostomy appliance according to the invention may be an open or a closed appliance suitable for use in connection with a colostomy, an ileostomy or a urostomy. The appliance may be a one-piece appliance or a body side member or faceplate forming part of a two-piece appliance comprising the body side ostomy member with a hole for the ostomy and a separate collection bag. The adhesive composition of the invention may be used for attaching a body side member of a one-piece or two-piece appliance to the abdomen of a patient and for sealing in-between the hole in the body side member and the ostomy.

A separate collection bag may be attached to the body side member in any convenient manner known per se, e.g. via a coupling ring or by a flange covered with an adhesive.

In a further aspect, the invention relates to an ostomy appliance comprising an adhesive wafer having a surface constituted by an adhesive composition of the invention containing a rubbery elastomeric matrix and one or more water soluble or water swellable hydrocolloids. Suitably, such an adhesive composition of the invention comprises a substantially homogeneous mixture of 25-60% of one or more polyisobutylenes, 3-35% of one or more styrene block copolymers comprising polyisobutylene blocks, and 20-60% of one or more hydrocolloids.

An ostomy appliance according to the invention may be made from materials conventionally used for the preparation of ostomy appliances and in a manner known per se in the field and the adhesive composition of the invention may be used as any other adhesive composition used in connection with attachment of a body side member to the patient and sealing around the ostomy.

In a preferred embodiment of the invention, the adhesive composition is the adhesive component in a "Swiss roll" adhesive useful for ostomy appliances of the kind disclosed in WO 89/05619, the other, more absorbing, component being a mixture of a suitable adhesive, preferably a PIB-based adhesive containing a hydrocolloid.

The invention also relates to a wound dressing comprising an adhesive composition as described above.

Thus, the invention relates to a wound dressing for covering e.g. a wound, an abrasion, a blister, a crack or a corn comprising an adhesive composition of the invention containing one or more water soluble or water swellable hydrocolloids. The adhesive composition useful for wound dressings is suitably a substantially homogeneous mixture of 25-60% of one or more polyisobutylenes, 3-35% of one or more styrene block copolymers comprising polyisobutylene block(s), and 20-60% of one or more hydrocolloids. The dressing is suitably covered by a top layer or a film.

The top layer or film is suitably a water impervious layer or film and may be of any suitable material known per se for use in the preparation of wound dressings e.g. a foam, a non-woven layer or a polyurethane, polyethylene, polyester or polyamide film.

The water impervious layer or film is preferably a low-friction flexible polymer film reducing the risk of unwanted stress in the area of the crack impeding the healing of a crack on a very exposed site.

A suitable material for use as a water impervious film is a polyurethane material.

A preferred low friction film material is disclosed in U.S. Pat. No. 5,643,187.

A preferred thickness of this film is below 20 microns, more preferred about 12-18 microns, resulting in a significant decrease of the modulus as compared to a film that is normally used when preparing medical dressings giving an improved stretch ability and adaptability of the dressing.

In a further aspect, the invention relates to a method for attaching an ostomy appliance for use in collecting discharge of visceral contents on the abdomen of a patient, said method comprising locating the stoma and an ostomy appliance comprising an adhesive wafer having a surface constituted by an adhesive composition according to the invention, optionally providing a hole in the adhesive wafer corresponding to the size and shape of the stoma and placing the adhesive wafer on the abdomen in sealing contact with the skin and the stoma.

In a still further aspect, the invention relates to a method for attaching a wound dressing to the skin of a patient, said method comprising locating the wound and a wound dressing comprising an adhesive composition having a surface constituted by an adhesive composition according the invention, and placing the wound dressing on the skin of the patient so as to cover the wound and the skin in a zone along the perimeter of the wound.

DESCRIPTION OF THE PREFERRED EMBODIMENTS

The invention is now explained more in detail with reference to the below working examples elucidating preferred embodiments of the invention.

Materials and Methods

SIBSTAR 073T: Styrene-isobutylene-styrene block copolymer from Kaneka Corporation having a molecular weight Mw=65,000, St=30 wt %.

SIBSTAR 102T: Styrene-isobutylene-styrene block copolymer from Kaneka Corporation having a molecular weight Mw=100,000, St=15 wt %.

SIBSTAR 103T: Styrene-isobutylene-styrene block copolymer from Kaneka Corporation having a molecular weight Mw=100,000, St=30 wt %.

SIBSTAR 042D: Styrene-isobutylene block copolymer from Kaneka Corporation having a molecular weight Mw=45,000, St=15 wt %.

PIB: Polyisobutylene available under the trademark Vistanex from Exxon Chemical Co. as grade LM-MH.

Kraton D1161: Styrene-isoprene-styrene (SIS) copolymer from Kraton Polymers UK Ltd having a molecular weight Mw of 212,000-260,000 (GPC) and a content of diblock 15-25%.

Arkon P90: A saturated alicyclic hydrocarbon resin from Arakawa Chemical Industries having a molecular weight 570 and a softening point of 90° C.
Paraffin oil: PL 500 from Parafluid Mineral Oel
CMC: Sodium carboxymethylcellulose available from Hercules under the trade name Blanose 9H4XF or from Akzo under the trade mark Akucell® AF2881
Dioctyl adipate, a plasticizer from International Speciality Chemicals Ltd.
Dioctyl phthalate, a plasticizer from International Speciality Chemicals Ltd
A Z mixer Type LKB 025 from Herman-Linden was used.

Example 1 and Comparative Example 1

The clarity of a film of a polymer composition according to the invention and the clarity of a film of a polymer composition according to the state of the art having the compositions stated in the below Table 1, were compared visually.

TABLE 1

| Ingredient in percent by weight | Example No. | |
|---|---|---|
| | 1 | Comp 1 |
| SIBSTAR 073T | 50 | |
| SIS | | 50 |
| PIB | 50 | 50 |
| Total | 100 | 100 |

Preparation of the Adhesive Compositions:
100 grams of Kraton® D1161 or SIBSTAR 073T was added to a Z mixer at 160° C. and softened for 5 minutes. Then 100 grams of PIB was added and mixing was continued at 150° C. and 50 mbar until the blend was homogeneous.

While still hot and soft, the resulting dough-like mass was then removed from the mixer and formed into a film material having a thickness of approximately 0.2 mm by compression moulding the adhesive mass at approximately 110° C. and 100 Bar between two sheets of silicone release paper.

The appearance of the film of Example 1 was clear whereas the appearance of the film of Comparative Example 1 was opaque.

Examples 2-4 and Comparative Examples 2-3

Determination of water absorption, erosion and gel strength for adhesive compositions according to the invention and adhesive compositions according to the state of the art.

Compositions according to Examples 2-4 are according to the invention and the composition according to Comparative Examples 2 and 3 are according to the state of the art and are stated in the below table 2.

TABLE 2

| Ingredient in percent by weight | Example No. | | | | |
|---|---|---|---|---|---|
| | 2 | Comp 2 | Comp 3 | 3 | 4 |
| SIBSTAR 102T | | | | 25 | 18 |
| SIBSTAR 073T | 25 | | | | |
| SIS | | 25 | 25 | | |
| PIB | 25 | 25 | 40 | 40 | 47 |
| Paraffin Oil | 15 | 15 | | | |
| CMC | 35 | 35 | 35 | 35 | 35 |
| Total | 100 | 100 | 100 | 100 | 100 |

Preparation of the Adhesive Compositions:
100 grams of Kraton® D1161, SIBSTAR 102T or SIBSTAR 073T was used and the amounts of other ingredients used correspond to the composition stated in Table 2.

Equal amounts of Kraton® D1161 SIBSTAR 102T or SIBSTAR 073T and Vistanex® LM-MH were mixed in a Z Mixer for 20 minutes at 160° C. under a vacuum of 100 mbar. Then, the vacuum was released, the mixing was continued at 160° C. for 10 minutes and the remains of Vistanex® LM-MH, and PL 500 were added and mixed for 10 minutes each. Then, the mixture was cooled to 90° C. Finally, CMC was added at a temperature of 90° C. under a vacuum of 100 mbar and mixed for 10 minutes.

While still hot and soft, the resulting dough-like mass was then removed from the mixer and formed into a sheet stock material having a thickness of approximately 1 mm by compression moulding the adhesive mass at approximately 90° C. and 100 Bar between two sheets of silicone release paper. The resultant flat plate was cut into the desired shapes.

Determination of Water Absorption.
Pieces of adhesive of 1×25×25 mm were immersed in 9% NaCl demineralised water at 37° C. and removed and weighed after 30, 60, 90, 120, 240, and 1440 hours. The percentage change in weight is recorded. The results appear from the below table 3.

TABLE 3

| Weight of specimen in percent of initial weight after immersion | | | | | |
|---|---|---|---|---|---|
| Time (min.) | Example | | | | |
| | 2 | Comp 2 | Comp 3 | 3 | 4 |
| 30 | 133 | 137 | 112 | 110 | 107 |
| 60 | 178 | 199 | 140 | 142 | 151 |
| 90 | 211 | 257 | 164 | 153 | 188 |
| 120 | 234 | 295 | 185 | 168 | 215 |
| 240 | 316 | 446 | 261 | 222 | 311 |
| 1440 | 538 | 869 | 723 | 481 | 793 |

A comparison of SIBS and SIS based compositions (example 2 with comparative example 2, and example 3 with comparative example 3) shows that similar absorption rates are achieved initially but on prolonged immersion, the absorption of compositions comprising SIBS slows down. This is believed to be due to increased cohesion or barrier properties of SIBS compositions, preventing a continuing deteriorating process due of increased water content.

Determination of Deterioration.
A disk of the adhesive having a thickness of 1 mm, an outer diameter of 50 mm and a hole of diameter of 15 mm was coated on the top surface with an impermeable film of LDPE. The exposed surface was attached to the surface of a petri dish. The adhesive and dish were left at 37° C. for 24 hrs. Then the dish was filled with 9% NaCl demineralised water. The whole adhesive specimen was covered by water.

The dish was then covered with a plastic sheet and left at 37° C. for 24 hrs. The diameters of the inner hole and outer edge were measured.

Deterioration was shown by an inner diameter less than 15 mm, and an outer diameter of greater than 50 mm. The results appear from the below table 4.

TABLE 4

Dimension of hole and outer diameter of disk in millimetres

| Example | 2 | Comp 2 | Comp 3 | 3 | 4 |
|---|---|---|---|---|---|
| Diameter hole | 12 | 11 | 11 | 12 | 12 |
| Diameter disk | 56 | 59 | 56 | 52 | 55 |
| % shrinkage hole | 20 | 27 | 27 | 20 | 20 |
| % expansion, disc | 12 | 18 | 12 | 4 | 10 |

The compositions comprising SIBS show improved resistance against deterioration over state of the art compositions comprising SIS. This is especially useful in applications where larger amounts of fluid are to be handled, e.g. in connection with ostomy appliances and wound dressings for exuding wounds. Thus, compositions comprising SIBS would provide further safety and wear time.

Determination of Gel Strength.

A disc of the adhesive at 1 mm thickness with a diameter of 50 mm was attached to the surface of a petri dish and the other surface of the disk was exposed. The adhesive and dish were left at 37° C. for 24 hrs. Then, the dish was filled with 9% NaCl demineralised water. The whole adhesive specimen was covered by water. The dish was then covered with a plastic sheet then left at 37° C. for 24 hrs. The increase of diameters of the discs, appearance of the discs was evaluated visually and rated "+" for no change and "−" for change of shape, surface smoothness and cohesive strength by scratching with a finger were noted. The last two parameters were given an arbitrary rating of 1 to 5, with 1 being the best.

The compositions comprising SIBS showed overall improved gel strength. This is especially useful in applications where larger amounts of fluid are to be handled. Compositions comprising SIBS would provide further safety and wear time as above.

The results appear from the below table 5.

TABLE 5

| Example | 2 | Comp 2 | Comp 3 | 3 | 4 |
|---|---|---|---|---|---|
| Increase of diameter in % | 0 | 52 | 20 | 0 | 12 |
| Disc Appearance | 3 | 3 | 3 | 3 | 2 |
| Smoothness | + | − | − | + | + |
| Strength | 2 | 1.5 | 2 | 1.5 | 2 |

The invention claimed is:

1. An ostomy appliance with an adhesive wafer comprising a water absorbent adhesive composition comprising a rubbery elastomeric matrix comprising:
   a) a styrene-isobutylene-styrene block copolymer, comprising from 15% to 30% polymerized styrene of the block copolymer and
   an unsubstituted polyalkylene homopolymer consisting of an unsubstituted polyisobutylene;
   b) one or more water-soluble or water swellable hydrocolloids; and
   c) does not include a tackifier.

2. The ostomy appliance with an adhesive wafer comprising the water absorbent adhesive composition according to claim 1 wherein the polymerized styrene has a molecular weight (Mw) between 1000 and 10000.

3. The ostomy appliance with an adhesive wafer comprising the water absorbent adhesive composition according to claim 1 wherein the homopolymer block consisting of polymerized isobutylene has a molecular weight (Mw) between 20000 and 100000.

4. The ostomy appliance with an adhesive wafer comprising the water absorbent adhesive composition according to claim 1 wherein the block-copolymer constitutes 1-70% by weight of the composition and wherein the =substituted polyalkylene homopolymer constitutes up to 70% by weight of the composition.

5. The ostomy appliance with an adhesive wafer comprising the water absorbent adhesive composition according to claim 1, wherein the one or more water-soluble or water swellable hydrocolloids constitutes 5-60% by weight of the composition.

6. The ostomy appliance with an adhesive wafer comprising the water absorbent adhesive composition according to claim 1 wherein the percent expansion of a disc prepared from the composition maintained at 37° C. for 24 hours is from 4 to 12%.

7. The ostomy appliance with an adhesive wafer comprising the water absorbent adhesive composition according to claim 1 wherein the weight percentage change of initial weight to final weight of the composition after immersion in 9 percent sodium chloride in demineralized water at 37° C. for 1440 minutes is from 481 to 538 percent.

8. An ostomy appliance with an adhesive wafer comprising a water absorbent adhesive composition comprising a rubbery elastomeric matrix consisting essentially of:
   a) a styrene-isobutylene-styrene block copolymer, comprising from 15% to 30% polymerized styrene of the block copolymer and an unsubstituted polyalkylene homopolymer consisting of an unsubstituted polyisobutylene; and
   b) one or more water-soluble or water swellable hydrocolloids;
   c) does not include a tackifier.

9. The ostomy appliance with an adhesive wafer comprising the water absorbent adhesive composition according to claim 8 wherein the polymerized styrene has a molecular weight (Mw) between 1000 and 10000.

10. The ostomy appliance with an adhesive wafer comprising the water absorbent adhesive composition according to claim 8 wherein the homopolymer block consisting of polymerized isobutylene has a molecular weight (Mw) between 20000 and 100000.

11. The ostomy appliance with an adhesive wafer comprising the water absorbent adhesive composition according to claim 8 wherein the block-copolymer constitutes 1-70% by weight of the composition and wherein the unsubstituted polyalkylene homopolymer constitutes up to 70% by weight of the composition.

12. The ostomy appliance with an adhesive wafer comprising the water absorbent adhesive composition according to claim 8 wherein the one or more water-soluble or water swellable hydrocolloids constitutes 5-60% by weight of the composition.

13. The ostomy appliance with an adhesive wafer comprising the water absorbent adhesive composition according to claim 8 wherein the percent expansion of a disc prepared from the composition maintained at 37° C. for 24 hours is from 4 to 12%.

14. The ostomy appliance with an adhesive wafer comprising the water absorbent adhesive composition accordto claim 8 wherein the weight percentage change of initial weight to final weight of the composition after immersion in 9 percent sodium chloride in demineralized water at 37° C. for 1440 minutes is from 481 to 538 percent.

15. The ostomy appliance with an adhesive wafer comprising the water absorbent adhesive composition according to claim 1 wherein styrene-isobutylene-styrene block copolymer has a Mw of from 65,000 to 100,000.

16. The ostomy appliance with an adhesive wafer comprising the water absorbent adhesive composition according to claim 8 wherein styrene-isobutylene-styrene block copolymer has a Mw of from 65,000 to 100,000.

17. The ostomy appliance with an adhesive wafer comprising the water absorbent adhesive composition according to claim 1 wherein the weight percentage change of initial weight to final weight of the composition after immersion in 9 percent sodium chloride in demineralized water at 37° C. for 1440 minutes is 481 percent.

18. The ostomy appliance with an adhesive wafer comprising the water absorbent adhesive composition according to claim 1 wherein the weight percentage change of initial weight to final weight of the composition after immersion in 9 percent sodium chloride in demineralized water at 37° C. for 1440 minutes is 538 percent.

19. The ostomy appliance with an adhesive wafer comprising the water absorbent adhesive composition according to claim 8 wherein the weight percentage change of initial weight to final weight of the composition after immersion in 9 percent sodium chloride in demineralized water at 37° C. for 1440 minutes is 481 percent.

20. The ostomy appliance with an adhesive wafer comprising the water absorbent adhesive composition according to claim 8 wherein the weight percentage change of initial weight to final weight of the composition after immersion in 9 percent sodium chloride in demineralized water at 37° C. for 1440 minutes is 538 percent.

21. The ostomy appliance with an adhesive wafer comprising the water absorbent adhesive composition according to claim 1 wherein the styrene-isobutylene-styrene block copolymer is present in the composition at 25% by weight and the unsubstituted polyisobutylene is present in the composition at 25% by weight.

22. The ostomy appliance with an adhesive wafer comprising the water absorbent adhesive composition according to claim 1 wherein the styrene-isobutylene-styrene block copolymer is present in the composition at 25% by weight and the unsubstituted polyisobutylene is present in the composition at 40% by weight.

23. The ostomy appliance with an adhesive wafer comprising the water absorbent adhesive composition according to claim 8 wherein the styrene-isobutylene-styrene block copolymer is present in the composition at 25% by weight and the unsubstituted polyisobutylene is present in the composition at 25% by weight.

24. The ostomy appliance with an adhesive wafer comprising the water absorbent adhesive composition according to claim 8 wherein the styrene-isobutylene-styrene block copolymer is present in the composition at 25% by weight and the unsubstituted polyisobutylene is present in the composition at 40% by weight.

* * * * *